United States Patent [19]

Kleiner et al.

[11] 3,941,752

[45] Mar. 2, 1976

[54] FLAME RETARDING LINEAR POLYESTERS AND SHAPED ARTICLES THEREOF

[75] Inventors: Hans-Jerg Kleiner, Bad Soden, Taunus; Manfred Finke, Fischbach, Taunus; Ulrich Bollert, Diedenbergen, Taunus; Walter Herwig, Neuenhain, Taunus, all of Germany

[73] Assignee: Hoechst Aktiengesellschaft, Frankfurt am Main, Germany

[22] Filed: Sept. 13, 1974

[21] Appl. No.: 505,686

[30] Foreign Application Priority Data
Sept. 17, 1973 Germany............................ 2346787

[52] U.S. Cl......... 260/75 P; 260/75 S; 260/DIG. 24
[51] Int. Cl.² ........................................ C08G 63/18
[58] Field of Search........ 260/75 P, DIG. 24, 45.7 P

[56] References Cited
UNITED STATES PATENTS

| 3,092,606 | 6/1963 | Ruppert et al. .............. 260/75 P X |
| 3,169,944 | 2/1965 | Scott et al. ................... 260/75 P X |
| 3,853,819 | 12/1974 | Herwig et al. ..................... 260/75 P |

FOREIGN PATENTS OR APPLICATIONS 1,232,348  1/1967  Germany
1,196,971  11/1959  France

OTHER PUBLICATIONS

Henning, *Chemical Abstracts*, Vol. 67:3124n (1967).
Khairullin et al., *Chemical Abstracts*, Vol. 68:105,302g (1968).

*Primary Examiner*—Harold D. Anderson
*Assistant Examiner*—W. C. Danison, Jr.
*Attorney, Agent, or Firm*—Curtis, Morris & Safford

[57] ABSTRACT

Flame-repellant linear polyesters are obtained by incorporating by condensation phosphorus-compounds having the formula

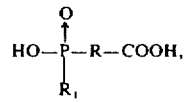

wherein R and $R_1$ are organic radicals which may also contain hereto atoms into the linear polyesters, preferably those from terephthalic acid and ethylene glycol. These polyesters are materials of which flame-repellent filaments, fibers, sheets, press-moulded and injection-moulded articles may be made. Products of the invention can be used whereever especially acute risks of ignition and fire exist.

8 Claims, No Drawings

FLAME RETARDING LINEAR POLYESTERS AND SHAPED ARTICLES THEREOF

It is an object of the present invention to provide flame retarded synthetic linear polyesters modified with carboxy-phosphinic acids, as well as articles shaped from these modified polyesters.

It is known that shaped articles, such as filaments and fibers can be prepared from linear polyesters which comprise in the polymer molecule phosphorus-containing compounds. In these cases, various acids of phosphorus and their derivatives were especially used as phosphorus-containing modification-compounds, e.g. also phosphonic acids and phosphinic acids. Thus, the German Auslegeschrift No. 1,243,819 describes filaments and fibers made from polyesters modified with phosphonic acid esters. The filaments and fibers are well suited for dyeing with basic and disperse dyestuffs and have a low pilling tendency.

Phosphonic and phosphinic acids or their esters are added in course of the processes for the preparation of fiber-forming linear polyesters, according to the disclosures in German Offenlegungsschrift No. 1,520,079 and German Offenlegungsschrift No. 1,595,598, and incorporated into the polymer chains. The main purpose of this modification is also to improve the dyeing properties of the corresponding filaments and fibers, and improvement in dyeing properties is the sole purpose of the polyester modification with bis-(p-carboxyphenyl)-phosphinic acid described by German Auslegeschrift No. 1,232,348.

However, it is also known that polyesters comprising phosphorus-containing compounds may have flame-repellent properties. Thus, French Pat. No. 1,196,971 discloses copolyesters having phosphonic acid units, and being resistant to flames and heat. These copolyester products can be used as flame-protection agents, adhesives, varnish and impregnating substances for paper and textiles as well as intermediate products. On the other hand, it is not possible to spin these polyesters to yield filaments or fibers, since their phosphorus content imparts brittleness to the products.

Furthermore, it has been suggested that flame-repellent polyesters be prepared by incorporating by condensation into the polyester molecules alkylene-diphosphinic acids, arylene-di-phosphinic acids or aralkylene-di-phosphinic acids which may also contain additional hetero atoms such as F, Cl, Br, O and S. These polyesters can be worked up to filaments, fibers and to shaped articles (German Offenlegungsschrift Nos. 2,236,037, 2,328,343, 2,236,038 and 2,236,039). But, due to their occasionally rather considerable volatility at the condensation temperatures, it is quite difficult to incorporate the diphosphinic acids by condensation. Therefore, non-volatile oligomers of diphosphinic acids with diols are often used and incorporated in the polyester by condensation. In such cases it is, of course, necessary to first prepare the oligomers.

Another method for preparation of flame-repellent polyesters has also been plasticized which involves incorporating phosphorus compounds into the polyester in such a way that they are not built into the polymer chains. According to the two Japanese Pat. Nos. 7,142,230 and 7,142,231 certain esters of phosphoric acid and halogen-containing aromatic dihydroxy-compounds have been used as such additives and according to Belgian Pat. No. 769,229 special polyphosphonates and poly(phosphonate-phosphates) have been similarly used. While the use of these additives provides good flame-protection properties, the flame-protection is not permanent and the products are subject to certain other disadvantages. These advantages are especially a consequence of the considerable tendency of the additives to migrate as a result of which the polymer products have a certain toxicity and the additives can be washed out relatively easily, e.g. in the course of dry cleaning of articles made of corresponding fibers. When the additives are washed out of the articles, the polymer products, of course, lose their flame-repellent properties.

In the course of the preparation of such fibers, the additives are often responsible for sticking together of the polymer chips during the drying process, as a consequence of the additives tending to migrate to the surface of the polymer chips. The quite highly-viscous polymer additives described in Belgian Pat. No. 769,229 have a viscosity such that mixing them homogeneously with the polyesters is rather difficult. Moreover, they cause undesirably high diglycol contents in cases where the additives are blended in while the polyester-forming reaction is still going on.

A comparison of these polymers with polymers in which, phosphorus compounds are incorporated into the chain molecules shows the polymers with the additives in question have poorer dyeing properties. Even red phosphorus has been used as an additive for producing flame-repellent and self-extinguishing properties of polyester fibers and filaments (German Offenlegungsschrift No. 2,148,348).

Even though such filaments and fibers are sufficiently flame-repellent or self-extinguishing, the addition of red phosphorus does not permit white products to be obtained. Thus the products obtained are of limited use only.

Therefore, it is an object of the present invention to produce permanently flame-retarding linear polyesters by using an appropriate modify agent which imparts flame-repellent properties to filaments and fibers spun therefrom the textile properties of which compare favorably with those of filaments and fibers made of the corresponding non-modified polyesters, and which also permit a work-up to yield useful sheets and shaped articles. Moreover, the modification agent should not be volatile during the process of incorporation by condensation.

The problems outlined above have been solved by the modified linear polyesters of the present invention. These modified polyesters consist of dicarboxylic acid components and diol-components as well as of phosphorus-containing chain members and comprise phosphorus-containing chain members having structural units of the formula

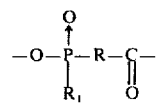

which constitute about 3 to 20 mol.% of the acid component of the polyester.

In this formula R is a saturated open-chained or cyclic alkylene-radical having from one to 15, preferably from two to 10 carbon atoms or an arylene or aralkylene-radical for example

—CH$_2$—, —CH$_2$—CH$_2$—, —(CH$_2$)$_3$—,

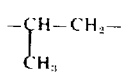

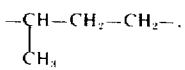

—(CH$_2$)$_4$—,

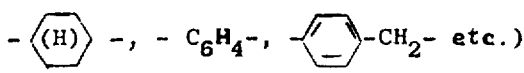

and R$_1$ is an alkyl radical having up to six carbon atoms, an aryl radical or an aralkyl radical for example
CH$_3$, C$_2$H$_5$, n- and i-C$_4$H$_9$, C$_5$H$_{11}$, C$_6$H$_{13}$, C$_6$H$_5$, C$_6$H$_5$-CH$_2$ etc.).

Preferred phosphorus-containing chain members are the structural units of the above formula with R being —CH$_2$—CH$_2$— or C$_6$H$_4$ and R$_1$ being CH$_3$ or C$_6$H$_5$, i.e.,

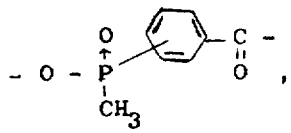

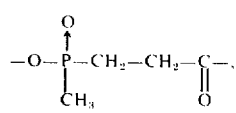

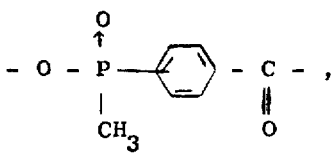

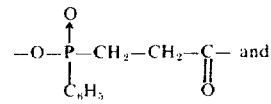

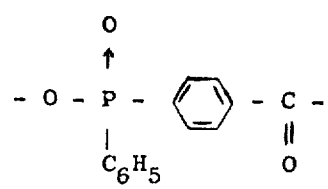

Radical R as well as radical R$_1$ may additionally comprise one or more hetero atoms, preferably halogen (F, Cl, Br) atoms, oxygen atoms or sulphur atoms; they may be located in branches or in the chain, the latter being preferred. "In the chain" means here a member of a chian consisting of carbon atoms. Due to their monovalence, halogen atoms cannot be located in the chain. Most suitable are O atoms and S atoms only. Though N-atoms are also possible chain members as —NH— or —NR'— groups (R' = an organic radical), they are less desirable, since N-compounds, as is well known to those skilled in the art are often responsible for producing undesirable discoloration in course of the polycondensation process.

Within the chain the S-atoms can be present as sulfide groups, sulfoxide groups or sulfone-groups, whereas on the chain or on the aromatic ring they may be present mainly as sulfonate groups.

The following examples may be cited to illustrate radicals R containing hetero atoms:

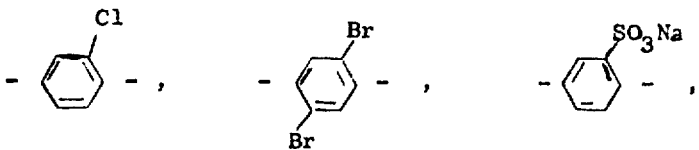

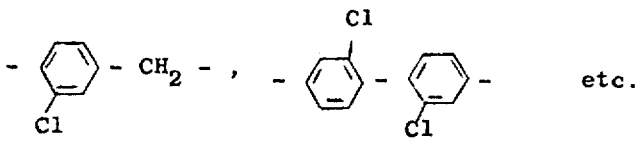

and with O atoms and S atoms in chain position.
—(CH$_2$)$_3$—O—(CH$_2$)$_3$-, —(CH$_2$)$_2$—O—(CH$_2$-)$_2$—O—(CH$_2$)$_2$—, —(CH$_2$)$_4$—O—(CH$_2$)$_4$-, —(CH$_2$)$_4$—S—(CH$_2$)$_4$—, —(CH$_2$)$_4$—S—(CH$_2$)$_4$—,

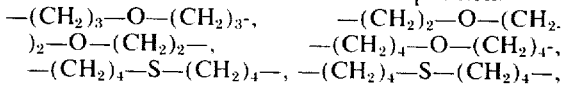

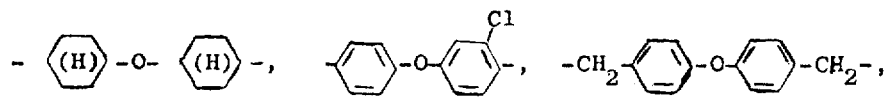

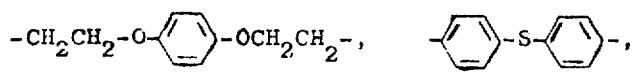

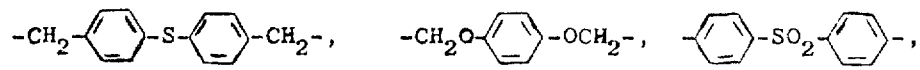

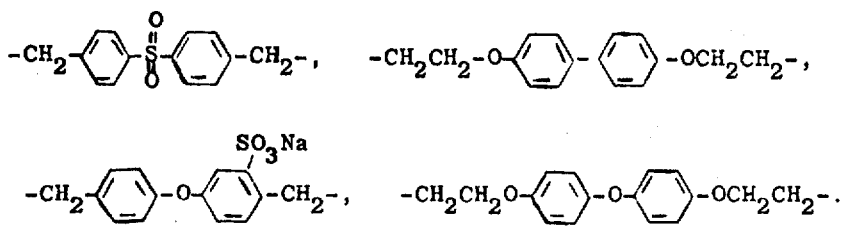

In cases where R is a saturated, open-chained or cyclic alkylene radical a halogen-substitution is satisfactory only, if the compounds either do not or only slightly yield hydrogen halide under the conditions used for preparation of the polyester. Suitable halogen-substituted alkylene radicals of this kind are, for example, the radical

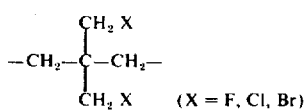

(X = F, Cl, Br)

or perfluorinated alkylene radicals.

Radical $R_1$ may also contain hetero atoms in similar manner. In this case, however, the most suitable substituents are halogen atoms or the sulfonate group, for example, $CH_2Cl$, $C_6H_4Cl$, $C_6H_4Br$, $C_6H_4SO_3Na$, etc.

The linear polyesters comprising the above, special structural units as chain members are obtained as follows: The usual starting materials which are known to be most suitable for preparing high-molecular and particularly fiber-forming and film-forming linear polyesters are reacted in known manner, while prior to, during or shortly before the end of the polycondensation bifunctional carboxy-phosphinic acids which may optionally contain further hetero atoms and/or their esters with a lower alcohol of especially from one to four carbon atoms or with diol are added, the latter also forming the diol component of the polyester. It is also possible to use the oligomers of the above carboxy-phosphinic acid-diol esters. It is further possible to use the cyclic anhydrides of phosphinic-carboxylic acids which form easily and are readily accessible. The quantity of the carboxy-phosphinic acid component may be from about 3 – 20 mol.% of the total acid component.

The carboxy-phosphinic acids used here have the formula

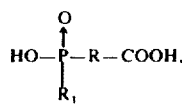

wherein R and $R_1$ have the aforesaid meaning.

The dicarboxylic acids used as starting materials may be free acids or may be esterified with lower aliphatic alcohols having preferably from one to four carbon atoms, especially $CH_3OH$, Terephthalic acid is preferred and may be used with other dicarboxylic acids as co-components. Other suitable acids are, for example, isophthalic acid, 5-sulfo-isophthalic acid, 5-sulfopropoxy-isophthalic acid, naphthalene-2,6-dicarboxylic acid, diphenyl-p, p-dicarboxylic acid, p-phenylenediacetic acid, diphenyloxide-p, p'-dicarboxylic acid, diphenoxy-alkane-dicarboxylic acids, transhexahydroterephthalic acid, adipic acid, sebacic acid, 1,2-cyclobutane-dicarboxylic acid etc.

Suitable diol-components are, besides ethyleneglycol, e.g. propane-diol-1,3, butane-diol-1,4 and the higher homologues of butane-diol-1,4 as well as, 2,2-dimethyl-propanediol-1,3, 1,4-cyclohexane-dimethanol etc., as well as co-components.

In cases where terephthalic acid is used with additional dicarboxylic acids as disclosed above, it is preferable that the additional acid constitute not much more than 10 mol.% of the total acid used. Similar considerations apply to the composition of the diol component. For example, if further diols besides the ethylene-glycol are used as components, their quantity preferably should not substantially exceed 10 mol.% of the total diol component.

If the starting materials are free dicarboxylic acids and diols, the first step, as usual for these reaction partners, is the esterification, followed by polycondensation. If the starting materials are dicarboxylic acid esters, and especially dimethyl esters, instead of free dicarboxylic acids, the first step is also transesterification which is followed by polycondensation, each of these steps using the usual catalysts.

Of course usual additives (cross-linking agents, delusterants and stabilizers, nucleating agents, coloring agent and fillers etc.) can be added during the preparation of polyesters, in addition to the usual catalysts.

Bifunctional carboxyphosphinic acids which are added prior to, during or shortly before termination of the polycondensation and which contain still further hetero atoms, or their esters or their cyclic anhydrides can be prepared as follows:

Carboxyphosphinic acids having but one carbon atom inserted between the P-atom and the COOH-group are obtained, for example, according to the reaction described by H.G. Hennig and G. Hilgetag in *J. Prakt. Chem.* 29, 86 ff (1965), starting from α-Cl or α-Br-acetic acid alkyl esters and phosphonous acid alkyl esters. A carboxymethyl-phenyl-phosphinic acid having e.g. the formula

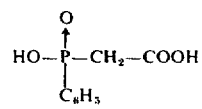

is obtainable by this method.

If R is an alkylene group having two or more carbon atoms, it is useful to follow the reaction scheme described by V. K. Chajrullin et al aprox. in *Z. Obsc. Chim.* 37 (1967) No. 3, pg. 710 – 714, starting from dichlorophosphines and unsaturated carboxylic acids, such as, for example:

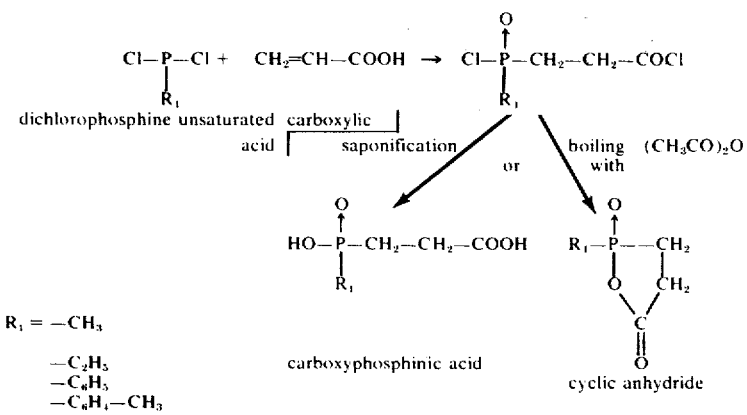

Among the unsaturated acids preference is given to the use of acrylic acid, methacrylic acid and crotonic acid.

Carboxyphosphinic acids having an aromatic radical (R = arylene) inserted between the P and COOH-groups can be prepared for instance according to the guidelines of the process described by L. D. Quin et al in *J. Org. Chem.* 27, 4120 (1962) or according to the process disclosed in Application serial No. (German Patent Application No. P 2346657.1) filed concurrently herewith.

That latter process consists in reacting halogenobenzoic acid esters with phosphoneous acid diesters according to the guidelines of an Arbusov reaction. The carboxylalkyl-phosphinic acid esters can be saponified e.g. by means of strong inorganic acids or bases.

Carboxyphosphinic acids with R being aralkylene can be prepared by analogy to Belgian Pat. No. 601,710 from carboxybenzylhalides and phosphoneous acid esters and subsequent saponification of the ester groups to yield free acids.

The carboxyphosphinic acids or their esters or cyclic anhydrides are not volatile under the conditions of the polyester-forming reaction — contrary to e.g. various diphosphinic acids — so that the former may be incorporated well and completely by condensation.

The phosphorus-organic structural unit is randomly distributed in the macromolecule of the polyester final product. Occasionally the carboxyphosphinic acid units may also be present as terminal groups, due to their random distribution. In order to guarantee the desired flame-repellent properties, moulding compositions should contain at least approx. 0,5 wt.% of phosphorus in the polyester, whilst the amount in filaments and fibers should be at least 1 wt.%. The flame-retarding qualities are further improved, if the P-containing chain members in the polyesters include halides as hetero atoms.

Subsequently, the completely condensed polyesters are spun to filaments and fibers as usual, stretched and submitted to additional treatment or extruded to yield sheets or, in known manner, worked-up to obtain shaped articles by press-moulding, injection-moulding or extrusion. Particularly suitable are filaments, fibers, sheets and shaped articles the dicarboxylic acid component of which contains mainly terephthalic acid and the diol component of which comprises essentially ethylene-glycol. All these shaped articles are also an object of the present invention.

The fibers and filaments have very good and permanent flame-repellent and self-extinguishing properties. Since they have a good degree of whiteness, they have very good dyeing properties for disperse dyestuffs and their receptivity includes acid dyestuffs in colour shades of average to deep intensity. If the P-containing chain members additionally include sulfonate groups, the receptivity also extends to basic dyestuffs. The diglycol portion of the polyesters increases only slightly. The tensile strength of the filaments and fibers, second order transition temperature, melting point, etc. approximately correspond to the values of the non-modified polyesters.

Such fibers and filaments are generally useful, for applications where readily ignitible textiles and technical articles cannot be tolerated, for example for awning cloths, carpets, curtains etc. It is also possible to use these filaments as one of the components in bi-component-filaments in combination with other polymers.

The sheets and shaped articles as well are used whereever serious risks of ignition and fire exist. If the transparency of the shaped articles is not a matter of concern, their solidity can be enhanced by imbedding therein e.g. inorganic fiber materials such as glass fibers, fibers from quartz, asbestos and carbon in the usual quantities. As examples of such shaped articles there can be cited casings, structural parts, electric machinery, mechanical transmission parts in automates, hollow articles, structural units in large-scale computers and sensitive electronic apparatus.

The following examples illustrate the present invention

EXAMPLE 1

1,000 g of dimethylterephthalate are transesterified with 720 ml of ethylene-glycol in the presence of 230 mg of manganacetate 4 H$_2$O as catalyst, the transesterification taking place under nitrogen at temperatures of from 170° - 220°C. After completion of the separation of methanol 100 g of 2-carboxy-ethyl-methylphosphinic acid (preparation according to V. K. Chajrullin et al, *Z. obsc.Chim* 37 (1967) No. 3, pg. 710 - 714) are added at 220°C and esterified.

After having added 350 mg of Sb$_2$O$_3$ the reaction mixture is further heated and, simultaneously, evacuated slowly so that a pressure of 1 torr at 250°C interior temperature is built up. The polycondensation is carried out at 0.2 torr and at 275°C until a relative viscosity (1 % solution in dichloroacetic acid at 25°) of 1,85 is attained. Melting point 244° - 248°C, phosphorus contents: 1.85 %.

The condensation product was spun from the melt under the usual conditions and, subsequently, stretched suitable for incorporation into polyester molecules. The following table shows the results.

TABLE

| Examples 2 – 8: Ex. No. | Modification agent | Preparation according to: | quantity added | rel.[+)] viscosity | characteristics of polyester melting point | P-content | Oxygen-test on tubular knit |
|---|---|---|---|---|---|---|---|
| 2 | 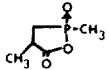 | V.K. Chajrullin et al. Z.obsc. Chim. 38 (1968) Nr. 2, S. 288–292 | 100 g | 1,75 | 240–242°C | 1,9 % | 30 Vol.% |
| 3 |  | V.K. Chajrullin et al. Z obsc. Chim. 37 (1967) Nr. 3, S. 710–714 | 80 g | 1,89 | 241–245°C | 1,6 % | 30 Vol.% |
| 4 |  | simultaneously filed Patent application no. P 23 46 657.1 our no. HOE 73/F 288 | 90 g | 1,54 | 243–245°C | 1,25 % | 28 Vol.% |
| 5 |  | | 100 g | 1,37 | 241–243°C | 1,4 % | 29 Vol.% |
| 6 |  | | 100 g | 1,81 | 247–249°C | 1,4 % | 29 Vol.% |
| 7 |  | V.K.Chajrullin et al. Z obsc. Chim. 37 (1967) Nr. 2, S. 455–460 | 125 g | 1,79 | 240–244°C | 1,7 % | 30 Vol.% |
| 8 | $C_2H_5-\overset{O}{\overset{\uparrow}{P}}-CH_2-CH_2-COOH$ with OH | V.K. Chajrullin et al. Doklady Akad. SSSR 162 (1965) Nr. 4, S 827–828 or Z obsc.Chim. 42 (1972) Nr. 8 S. 1730–1733 | 75 g | 1,77 | 245–247°C | 1,3 % | 27,5 Vol.% |

[+)]measured or carried out according to the description of Example 1 in a proportion of 1 : 3.65. The threads obtained showed a resistance of 33 g/tex at an elongation at break of 35 %. They were worked up to a tubular knit which was used for dyeing and flame tests.

Dyeing with the acid dyestuffs having the commercial names of

"Supranol Echtrot" (C.I. No. 24,790) (Red)
"Alphanol Echtblau FGLL" (C.I. No. 62,155) (Blue)
"Lanaperlgelb 3 G" (C.I. No. 19,025) (Yellow)
yielded deep colour shades.

The flammability test was carried out according to the oxygen-index method as per the test regulation ASTM D 2863-70. For that purpose the tubular knit was fitted vertically into the apparatus and flamed from above. An artificial oxygen/nitrogen atmosphere was created with a quantity of oxygen which was just enough to allow the test knit to burn.

A value of 29 vol.% of $O_2$ had been found. A corresponding tubular knit made of non-modified polyethylene-terephthalate started burning at an oxygen concentration of 20 vol.%.

EXAMPLES 2 – 8

The test according to example 1 was repeated with different carboxyphosphinic acids or their derivatives

EXAMPLE 9

The experiment as per example 1 was repeated, except that 6 mol.% of the DMT was replaced by dimethyl-isophthalate in the transesterification step. The polymer melting point was then 236° – 238°C. The relative viscosity was 1.82. Tubular knits made of this material have an oxygen index value of 30 %.

EXAMPLE 10

Example 1 was repeated with the difference that, instead of 100 g of 2-carboxy-ethyl-methyl-phosphinic acid there are used 75 g of its cyclic anhydride 2-methyl-2,5-dioxo-1-oxa-2-phospholane having formula

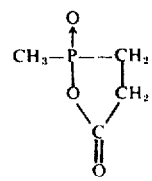

and, instead of 350 mg of $Sb_2O_3$ of example 1, the present example 10 used 300 mg of $GeHPO_3$.

The purely white polyester containing 1.5 % of phosphorus was crushed in the cold. The reduced specific viscosity of the granules was 1.08 (measured in phenol/tetrachloroethane = 3 : 2 at 25°C). The viscosity of the granules was increased to 1.36 by condensation of the solid matter in a rotating vessel at 230°C and at 0.2 torr, condensation period 8 hours.

The granules were worked up to plates on an injection moulding machine, the cylinder having temperatures of 260°/270°/260°C, the moulding temperature being 20°C. The plates measuring 60 × 60 × 2 mm were transparent and completely colorless, their reduced specific viscosity was 1.25. The impact strength of the plates was examined by means of the drop hammer test, exposing the plates to the vertical impact of a dropping object (drop hammer) from various heights, the plates being clamped onto a frame. The tip of the drop hammer was shaped as a hemisphere having a radius of 10 mm and a weight of 1 kg. For each height 10 plates were submitted to the test. For example, at a given dropping height of 150 cm the impact was strong enough to break 50 % of the plates. The impact strength of the plates of the example was 200 cm.

Plates being obtained under the same conditions but without the phosphorus modification compound and having a reduced specific viscosity of 1.32, showed an impact strength of 190 cm when submitted to impact under the same conditions.

For the flammability test the granules were pressed to plates 1.3 mm thick at a temperature between 230° and 250°C and under a pressure of 80 atm. From these plates were cut test specimens measuring 127 × 12.7 mm. The result of the flammability test according to ASTM D 635-68 was "non-ignitible," the flammability test being carried out according to Underwriters Laboratories (UL) Subject 94 "SE O."

EXAMPLE 11

Example 10 was repeated with the difference that instead of 75 g of 2-methyl-2,5-dioxo-1-oxa-2-phospholane only 35 g of this compound were used. The phosphorus portion was then 0.7 %. The flammability test according to ASTM D 635-68 showed the material to be "self-extinguishing."

We claim:

1. A linear polyester which is the polycondensation product of a dicarboxylic acid, a diol and a flame-retarding carboxy-phosphinic acid monomer, said monomer being used in an amount of from 3 to 20 mol percent, based on the total amount of dicarboxylic acid and monomer, said monomer being a source of structural units in said polyester of the formula

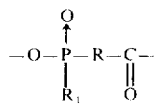

wherein R is saturated, open-chain or cyclic alkylene, arylene or aralkylene having one to 15 carbon atoms, and may contain one or more hetero atoms selected from F, Cl, Br, O and S, and $R_1$ is alkyl having up to six carbon atoms, aryl, or aralkyl and may contain one or more hetero atoms selected from F, Cl, Br, O and S, provided that in the R and $R_1$ groups the O, if present, is the oxygen of an ether group, and the S, if present, is the sulfur of a thioether, sulfoxide, sulfone or sulfonate group.

2. A linear polyester according to claim 1 wherein

R is —$CH_2$—$CH_2$— or —$C_6H_4$-and
$R_1$ is $CH_3$— or $C_6H_5$—.

3. A linear polyester according to claim 1 wherein the radical R or $R_1$ contains a hetero atom O or S.

4. A linear polyester according to claim 1 wherein the units derived from dicarboxylic acid are essentially terephthalic acid units and the units derived from the diol are essentially units of a diol of the formula
HO $(CH_2)_n$OH
wherein $n$ is 2 to 10, or the diol units are derived from 1,4-cyclohexane-dimethanol.

5. A linear polyester according to claim 1 wherein the units derived from dicarboxylic acid are essentially terephthalic acid units and the units derived from diol are essentially ethylene glycol units.

6. A method of making a linear polyester which comprises polycondensing a dicarboxylic acid or a lower alkyl ester thereof with a diol in the presence of a flame-retarding phosphorus containing monomer of the general formula

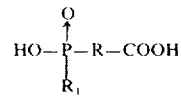

or a lower alkyl ester or cyclic anhydride of said monomer in an amount of about 3 to 20 mole percent of the total acid components wherein the symbol R of said formula is saturated, open-chain or cyclic alkylene having one to 15 carbon atoms, arylene or aralkylene, and $R_1$ of the formula is alkyl having up to 6 carbon atoms, aryl or aralkyl, and wherein R and $R_1$ may further contain one or more hetero atoms selected from F, Cl, Br, O and S, provided that in the R and $R_1$ groups the O, if present, is the oxygen of an ether group, and the S, if present, is the sulfur of a thioether, sulfoxide, sulfone or sulfonate group.

7. A process according to claim 6 wherein the dicarboxylic acid is terephthalic acid and the diol is ethylene glycol.

8. Shaped articles made by molding or extrusion of the linear polyester of claim 1.

* * * * *